United States Patent [19]
Ledley

[11] Patent Number: 5,639,669
[45] Date of Patent: Jun. 17, 1997

[54] SEPARATION OF FETAL CELLS FROM MATERNAL BLOOD

[76] Inventor: Robert Ledley, 1002 La Grande Rd., Silver Spring, Md. 20903

[21] Appl. No.: 486,501

[22] Filed: Jun. 7, 1995

[51] Int. Cl.$^6$ ................................................. G01N 1/18
[52] U.S. Cl. .................... 436/177; 422/101; 422/68.1; 436/910; 209/212; 209/213; 209/214; 209/223.1; 210/222; 210/223; 210/695; 210/282; 435/2
[58] Field of Search ................... 422/68.01, 101; 436/177, 910; 209/212, 213, 214, 223.1; 210/222, 223, 695, 282; 435/2

[56] References Cited

U.S. PATENT DOCUMENTS

| | | | |
|---|---|---|---|
| 3,838,773 | 10/1974 | Kolm | 209/223.1 |
| 4,054,513 | 10/1977 | Windle | 209/223.1 |
| 4,230,685 | 10/1980 | Senyei et al. | 424/12 |
| 4,675,286 | 6/1987 | Calenoff | 435/7 |
| 4,710,472 | 12/1987 | Saur et al. | 435/287 |
| 4,828,711 | 5/1989 | Cohen | 210/695 |
| 4,910,148 | 3/1990 | Sorensen et al. | 435/317.1 |
| 4,984,574 | 1/1991 | Goldberg et al. | 128/635 A |
| 5,130,027 | 7/1992 | Noble et al. | 210/695 |
| 5,153,117 | 10/1992 | Simons | 435/2 |
| 5,318,914 | 6/1994 | Matte et al. | 209/214 |
| 5,409,813 | 4/1995 | Schwartz | 435/7.24 |
| 5,411,863 | 5/1995 | Miltenyi | 435/6 |
| 5,432,054 | 7/1995 | Saunders et al. | 435/2 |
| 5,466,574 | 11/1995 | Liberti et al. | 209/223.1 |
| 5,489,386 | 2/1996 | Saunders | 210/514 |
| 5,498,550 | 3/1996 | Fujiwara et al. | 200/222 |
| 5,514,340 | 5/1996 | Lansdorp et al. | 209/223.1 |

OTHER PUBLICATIONS

D. Dale & F. Federman, Scientific American Medicine, 1996, pp. 8–10.

*Primary Examiner*—Jill Warden
*Assistant Examiner*—Sharidan Carrillo
*Attorney, Agent, or Firm*—Gary Steven Pisner

[57] ABSTRACT

It is often important for medical purposes to obtain nucleated fetal cells during pregnancy. For example, the procedures of amniocentesis or chrionic villae extraction are carried out for this purpose. But these methods are invasive, and carry a small but positive risk to the patient, and are complicated to perform. On the other hand, the purpose of my invention is to obtain nucleated fetal cells (fetal nucleated reticulocytes) from maternal blood, which eliminates the need for invasive methods. There are a small number of nucleated fetal red blood cells (reticulocytes) in maternal blood and my invention is a method and apparatus for separating these fetal cells from maternal blood.

Several methods have previously been proposed, involving fluorescent antibody antigen reactions (immunofluorescence), other antibody-antigen means, that depend on the difference between the cell walls of maternal and fetal blood cells, but all of these methods have been unsatisfactory because they have proved to be unreliable and expensive, and to involve some final additional technique to isolate the cells, such as flow cytometry. On the other hand, my invention does not use antibody-antigen means, but is based on the fundamental difference between maternal and fetal cells, namely that the former contains adult hemoglobin (HbA) while the latter contains fetal hemoglobin (HbF). The difference in the properties of these hemoglobin molecules themselves enables the fetal cells to be separated from the maternal cells by a magnetic field means.

18 Claims, 8 Drawing Sheets

SEPARATION OF FETAL CELLS FROM MATERNAL BLOOD

Background

It is often important for medical purposes to obtain nucleated fetal cells during pregnancy. For example, the procedures of amniocentesis or chrionic villae extraction are carried out for this purpose. But these methods are invasive, and carry a small but positive risk to the patient, and are complicated to perform. On the other hand, the purpose of my invention is to obtain nucleated fetal cells (fetal nucleated reticulocytes) from maternal blood, which eliminates the need for invasive methods. There are a small number of nucleated fetal red blood cells (reticulocytes) in maternal blood and my invention is a method and apparatus for separating these fetal cells from maternal blood.

Several methods have previously been proposed, involving fluorescent antibody antigen reactions (immunofluorescence), other antibody-antigen means, that depend on the difference between the cell walls of maternal and fetal blood cells, but all of these methods have been unsatisfactory because they have proved to be unreliable and expensive, and to involve some final additional technique to isolate the cells, such as flow cytometry. On the other hand, my invention does not use antibody-antigen means, but is based on the fundamental difference between maternal and fetal cells, namely that the former contains adult hemoglobin (HbA) while the latter contains fetal hemoglobin (HbF). The difference in the properties of these hemoglobin molecules themselves enables the fetal cells to be separated from the maternal cells by a magnetic field means.

Hemoglobin (Hb) is a tetrameric protein composed of four subchains, or globin monomers, each of which contains a heme group with an iron (Fe) atom at its center. The function of Hb is to carry oxygen ($O_2$) to body tissues, and depends on the binding of $O_2$ to the Fe in the heme group of each monomer. The iron is normally in the ferrous (Fe(II)) oxidation state whether or not the heme is oxygenated. The change from deoxygenated Hb (deoxyHb) to oxygenated Hb (oxyHb) involves a change in the electronic state of the Fe(II)-heme as indicated by the change in color of venous blood from the dark purplish hue to the brilliant red color of arterial blood. This change also explains why deoxyHb is paramagnetic, whereas oxyHb is non-paramagnetic.

My invention takes advantage of the main structural difference between nucleated adult and fetal red blood cells (rbc's), i.e., reticulocytes and erythrocytes, namely, the difference in the structure of the contained hemoglobin molecules. Maternal or adult hemoglobin (HbA) differs from fetal hemoglobin (HbF) in that the four subchains of HbA consist of two $\alpha$ chain monomers, and two $\beta$ chain monomers, whereas HbF is comprised of two $\alpha$ chain monomers and two $\gamma$ chain monomers. The result of this structural difference is that under normal physiologic conditions the $O_2$ affinity of HbF is greater than that of HbA, enabling the fetal rbc's to obtain $O_2$ from the maternal rbc's.

Figure 1:
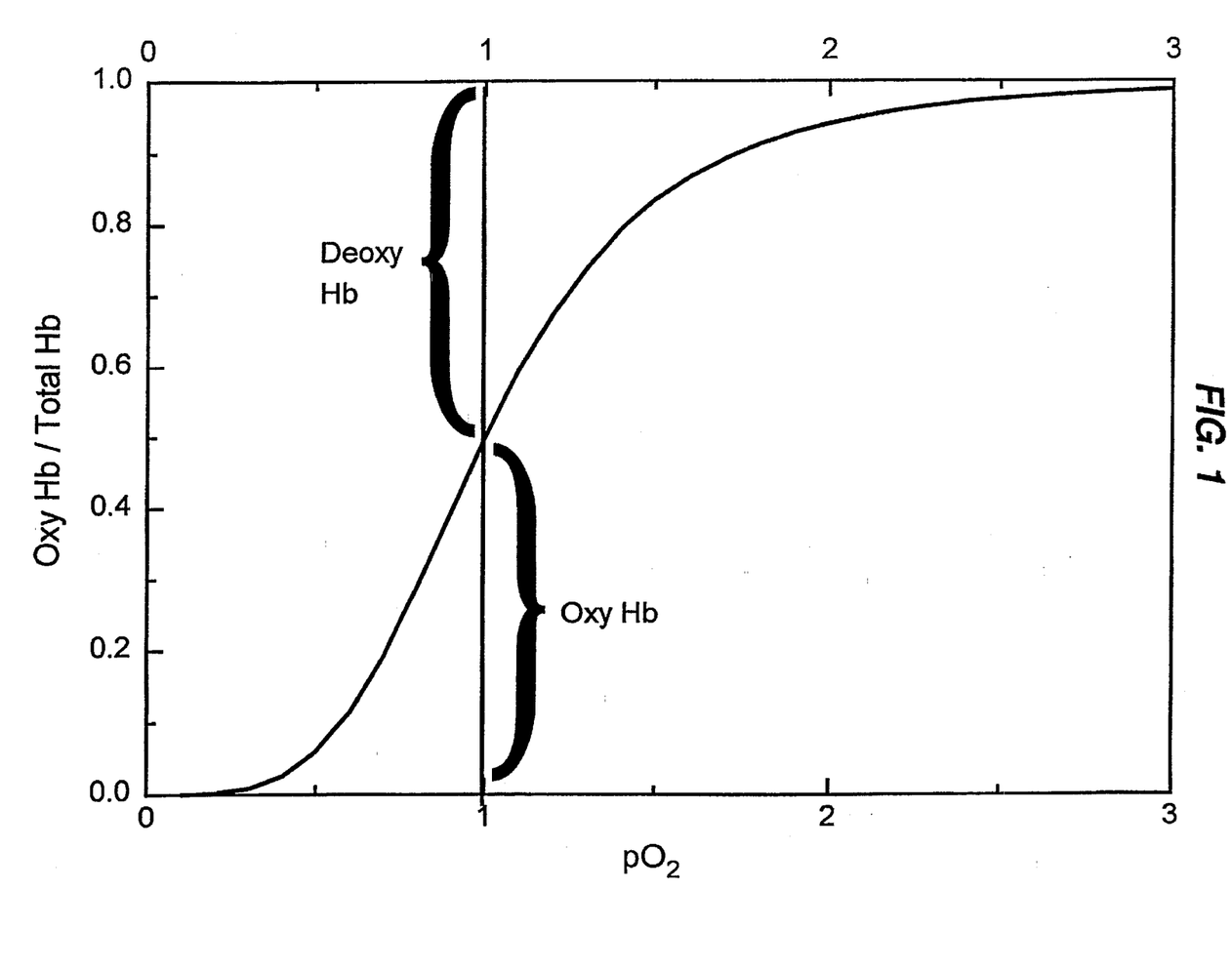
FIG. 1 is a Hill curve for hemoglobin giving the proportion of oxyhemoglobin as a function of $pO_2$ where the vertical line indicates for a particular $pO_2$ the proportion of oxyhemoglobin versus deoxyhemoglobin that would exist.

The affinity of Hb for $O_2$ is given by the Hill equation for the chemical reaction $[deoxyHb]+4[O_2] \leftrightarrows [oxyHb]$ with reaction rate constant $K=[deoxyHb][O_2]^4/[oxyHb]$, giving the fractional yield Y, namely $[oxyHb]/([deoxyHb]+[oxyHb])$, as a function of $[O_2]$ where $[O_2]$ is the partial pressure of $O_2$, usually denoted by $pO_2$:

$$Y=[pO_2]^4/(K+[pO_2]^4)$$

FIG. 1 shows the graph or Hill curve giving the yield of oxyHb as a function of the partial pressure of $pO_2$ (i.e., the concentration, $[_2]$).

Figure 2:
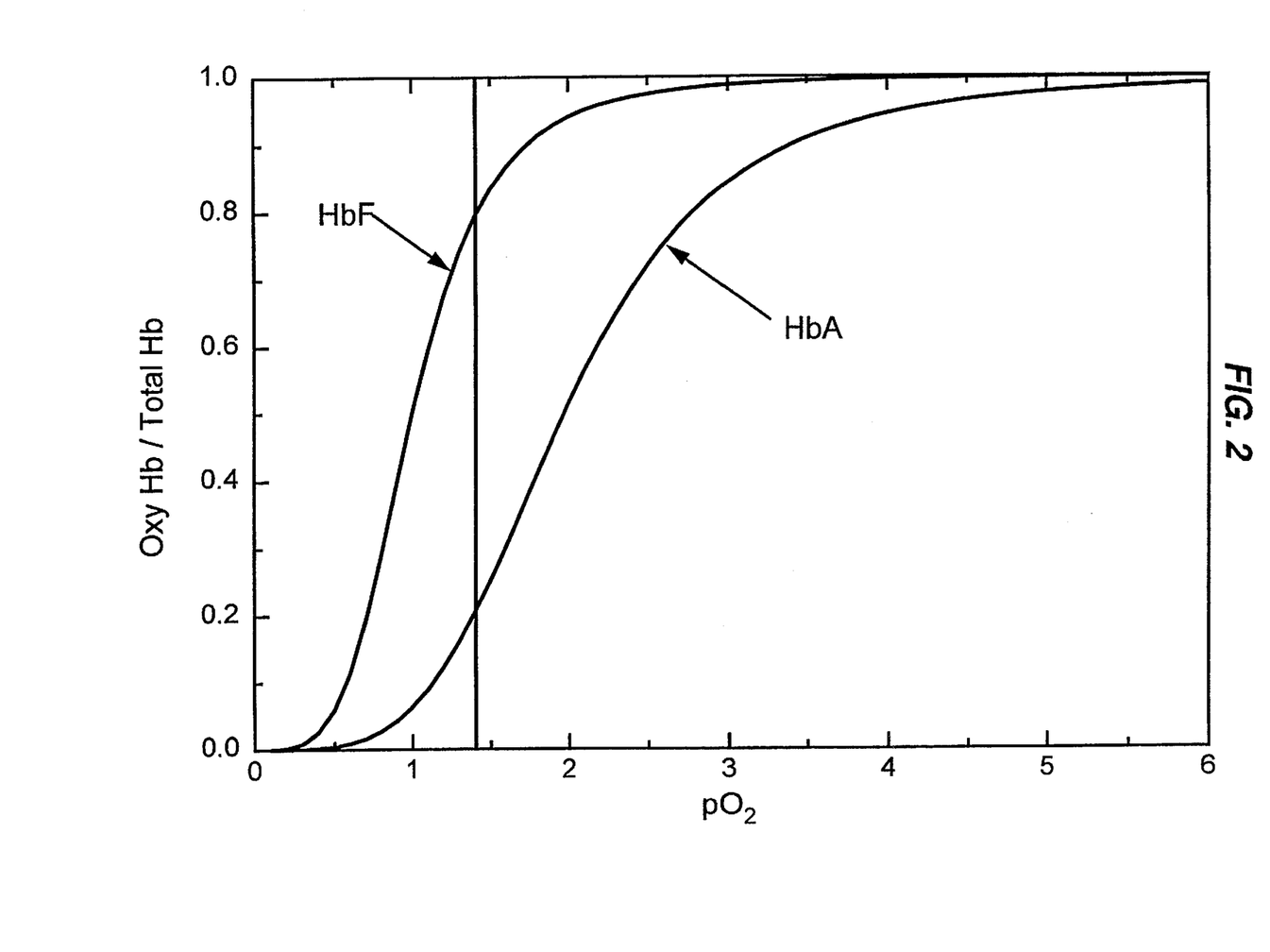
FIG. 2 are Hill curves for adult or maternal hemoglobin and for fetal hemoglobin where the vertical line indicates how for a particular $pO_2$ the proportion of oxyhemoglobin differs in maternal blood cells from that of fetal blood cells.

If we graph the curves for the yield Y of both oxyHbA and oxyHbF as a function of $pO_2$, as shown in FIG. 2, then it can be seen that at any given $pO_2$, the yield of oxyHbF is greater than that of oxyHbA (i.e., see for instance, the vertical line).

Figure 3:
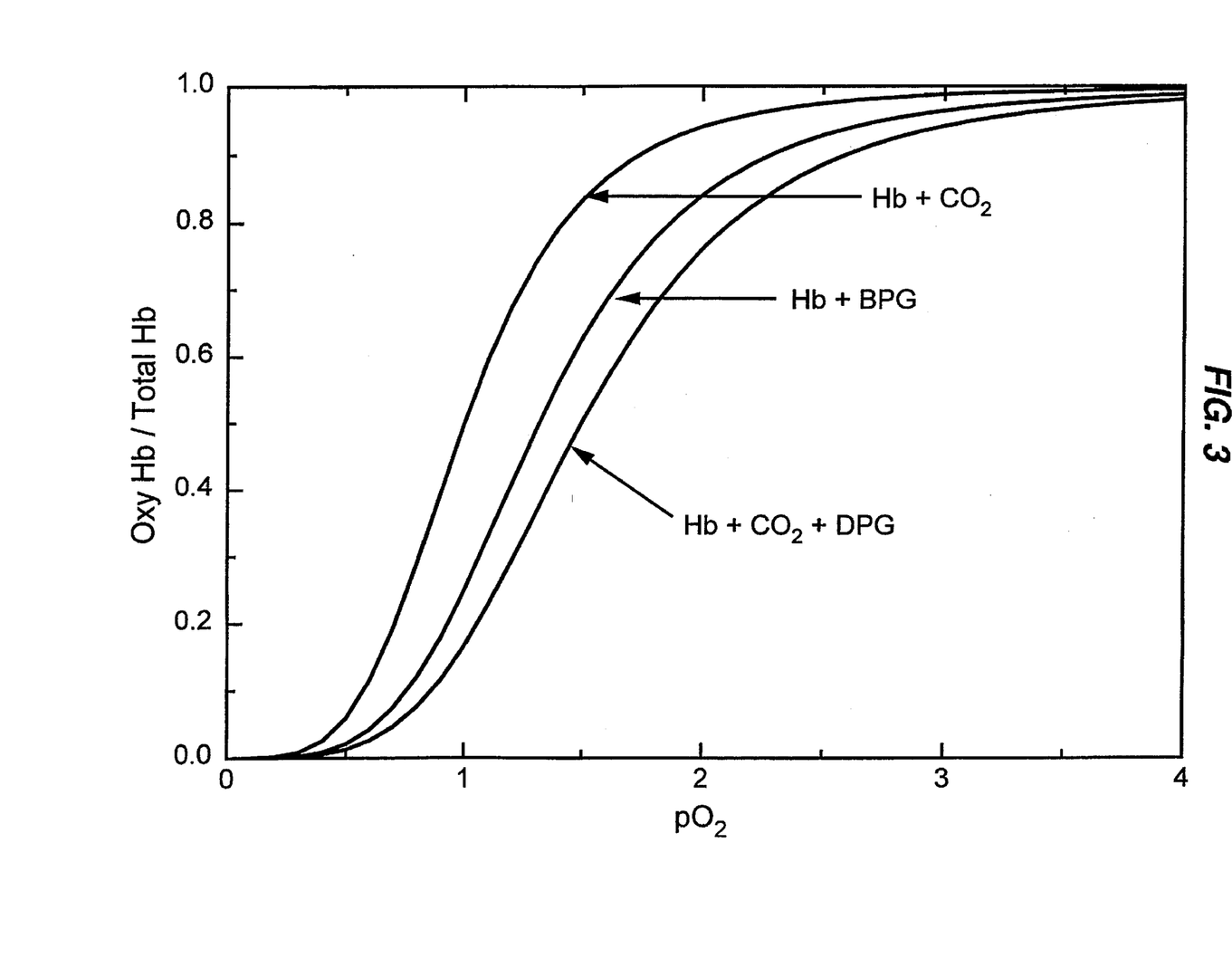
FIG. 3 gives Hill curves illustrating how various other chemical factors effect the curves.

Five physiologic factors can have an important influence on the curves, namely, the concentrations of $CO_2$, $H^+$, $Cl^-$ and D-2,3-bisphosphoglycerate (BPG), and the temperature (T). FIG. 3 shows the effect of combinations of some of these factors. In general it can be said that decreasing the concentrations of $CO_2$, $H^+$, $Cl^-$, and BPG will move the curve to the left, and make the maximum slope of the curve somewhat steeper. Decreasing the temperature will also move the curve to the left. Decreases in the concentrations of adenosine triphosphate (ATP) and inositol hexaphosphate (IHP) will have a similar effect, although these factors are not as important as the five just discussed.

In summary: (a) deoxyHb is paramagnetic whereas oxyHb is not; (b) five main factors can influence the $O_2$ affinity (or oxyHb yield curves), namely the concentrations of $CO_2$, $H^+$, $Cl^-$, and BPG, and the temperature T; and finally (c) HbF has a greater $O_2$ affinity than HbA under the same $pO_2$ condition. My invention makes use of these observations, combining them to produce a unique method and apparatus for separating fetal nucleated reticulocytes from maternal blood.

In particular, my invention takes advantage of the fact that, as can be seen from FIG. 2, at a particular value of $pO_2$, the yield of oxyHbF can be significantly greater than that of oxyHbA. The in-vitro manipulation of the various factors can enhance this effect. This means that Hb in the nucleated fetal cells, i.e., HbF, will mostly be oxyHbF, whereas Hb in the nucleated maternal cells, i.e., HbA, will mostly be deoxyHbA. In an applied magnetic field, the deoxyHbA will be affected by the field, whereas the oxyHbF will not. Thus the maternal cells containing the deoxyHbA will be effected by the magnetic field, whereas the fetal cells containing the oxyHbF will not. The magnetic field can then effectuate the separation of nucleated maternal from nucleated fetal cells by acting on the respective HbA but not the HbF within the respective cells.

Despite extensive research on Hb and on methods of identifying and separating fetal nucleated reticulocytes from maternal blood, no one has heretofore combined the above described observations to carry out such an identification and separation.

PREFERRED EMBODIMENT

Figure 4:
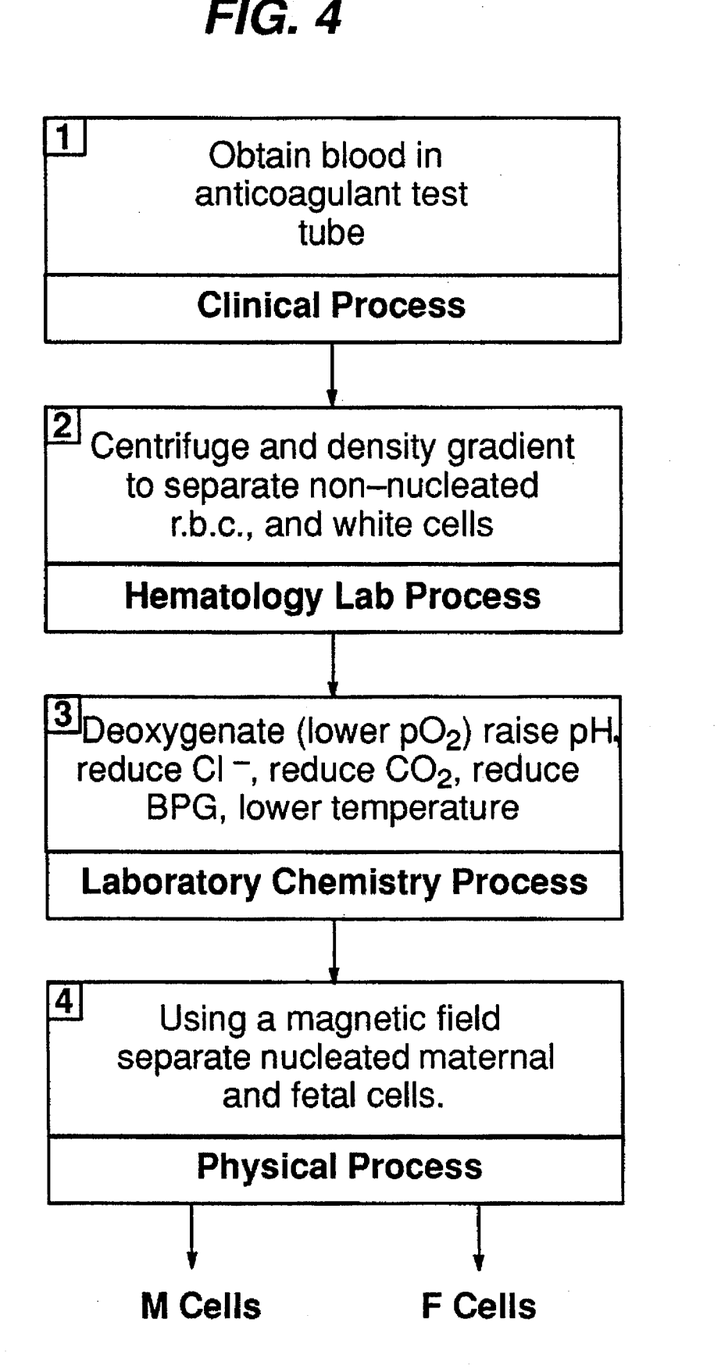
FIG. 4 is a block diagram of the four processes involved.

The method consists of four processes as shown in FIG. 4. The first process is to obtain the maternal blood from a pregnant woman in an anticoagulant test tube as is normally carried out by physicians for making general diagnostic blood tests. The second process can also be a standard hematology laboratory process in which, for example, the maternal blood is centrifuged in a density gradient to separate the non-nucleated red blood cells from the nucleated blood cells. Also, the hemoglobin in the nucleated rbc's could be stripped of $O_2$ and a magnetic field used to separate them from cells not containing hemoglobin, namely the white blood cells.

The third process involves the preparation of the maternal blood sample for insertion into the apparatus. First, the blood sample is preprocessed to remove undesirable cell types and contaminates using at least one of the methods selected from the following: removing from said specimen platelets and non-nucleated blood cells using standard medical laboratory means; removing from said specimen platelets, non-nucleated cells, and polymorphonuclear cells leaving mononuclear cells using standard medical laboratory means; separating the Hb containing cells from the other components of the said blood specimen using a deoxygenating means for removing the oxygen from the hemoglobin in the Hb containing blood cells of the said blood specimen, so that the Hb in the cells will contain mostly deoxyHb, followed by applying said magnetic field means for separating the Hb containing cells from the other components of the said blood specimen; and/or removing from said blood specimen platelets and non-nucleated cells, followed by deoxygenating means for removing the oxygen from the hemoglobin in the Hb containing blood cells of the said blood specimen, followed by applying said magnetic field means for separating the Hb containing cells from the other components of said blood specimen using standard medical laboratory means. The next step in the preparation of the blood involves a process of reducing the $O_2$ in the fluid containing the nucleated red blood cells in the test tube, raising the pH (i.e., reducing the $H^+$ concentration), reducing the $Cl^-$ concentration, reducing the $CO_2$ concentration, and lowering the temperature. This will produce the same effect inside the cells. Also the BPG inside the cells can be enzymatically reduced. The exact concentrations are chosen to approximately maximize the difference between the Hill curves for HbA and HbF as shown in FIG. 2. The pair of curves will vary with the concentrations of the aforementioned five factors, and for each such pair of curves there is a particular value of $pO_2$ at which there is a maximum ordinate difference between the curves. Thus a set of factors will be chosen such that this maximum ordinate difference is greatest, in order to maximize the magnetic force difference between the maternal nucleated cells containing HbA and the fetal nucleated cell containing HbF for the separation process when the magnetic field is applied.

Figure 5:
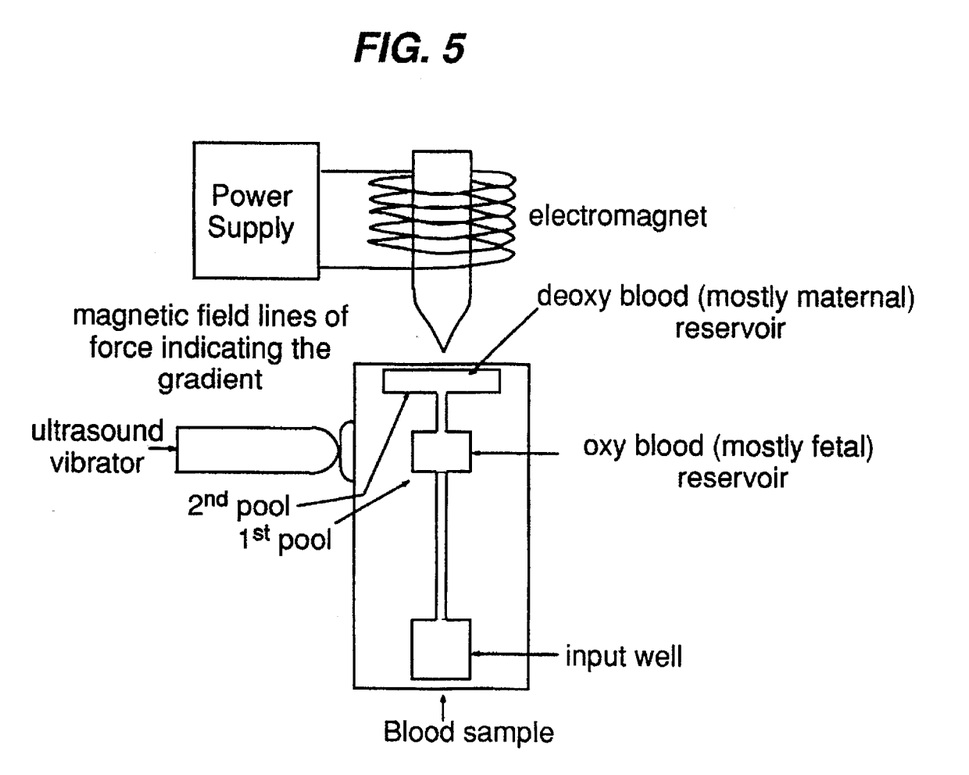
FIG. 5 is a diagrammatic drawing of the apparatus of the invention.

Once the sample has been prepared it is then inserted into the apparatus, and the fourth process consists of applying the magnetic field means to the blood sample to effectuate the separation of nucleated fetal cells from the maternal cells. The elements of the apparatus are shown in FIG. 5 and consists of a chamber with pools for blood movement, and an ultrasound vibrator to vibrate the slide, and an electromagnet and associated power supply to generate the magnetic field gradient required. The chamber will be made out of hydrophobic material to prevent the cells from sticking to the surfaces. The electromagnet will be constructed to have a point at one end in order to concentrate the lines of force to develop the maximum field gradient. The blood sample is placed in the input well. The electromagnetic will then be turned on generating the magnetic field gradient. In one embodiment of this invention, the magnetic field means is a magnet shaped to produce a magnetic field gradient coveting said chamber having the largest magnetic field magnitude of said gradient covering a second pool and the smallest said magnetic field magnitude of said gradient covers a first pool so that said blood cells affected by said magnetic field gradient will move through a second channel.

Since the maternal blood cells contain deoxyHbA, thereby being paramagnetic, the hemoglobin molecules contained therein will become naturally oriented in the direction of the magnetic field lines of force. The maternal cells will then move in the gradient field toward the tip of the electromagnet, leaving the fetal cells, containing oxyHbF, behind. The ultrasound vibrator will help prevent the cells from sticking to each other. The maternal cells will move through the first pool into the second pool whereas the fetal cells containing oxyHbF will remain in the first pool. The blood sample can then be withdrawn from the slide in two aliquots, one from the first pool and the other from the second pool, which we will denote as deoxyHbA #1 and oxyHbF #1, respectively. We denote this first separation process as S #1.

Figure 6:
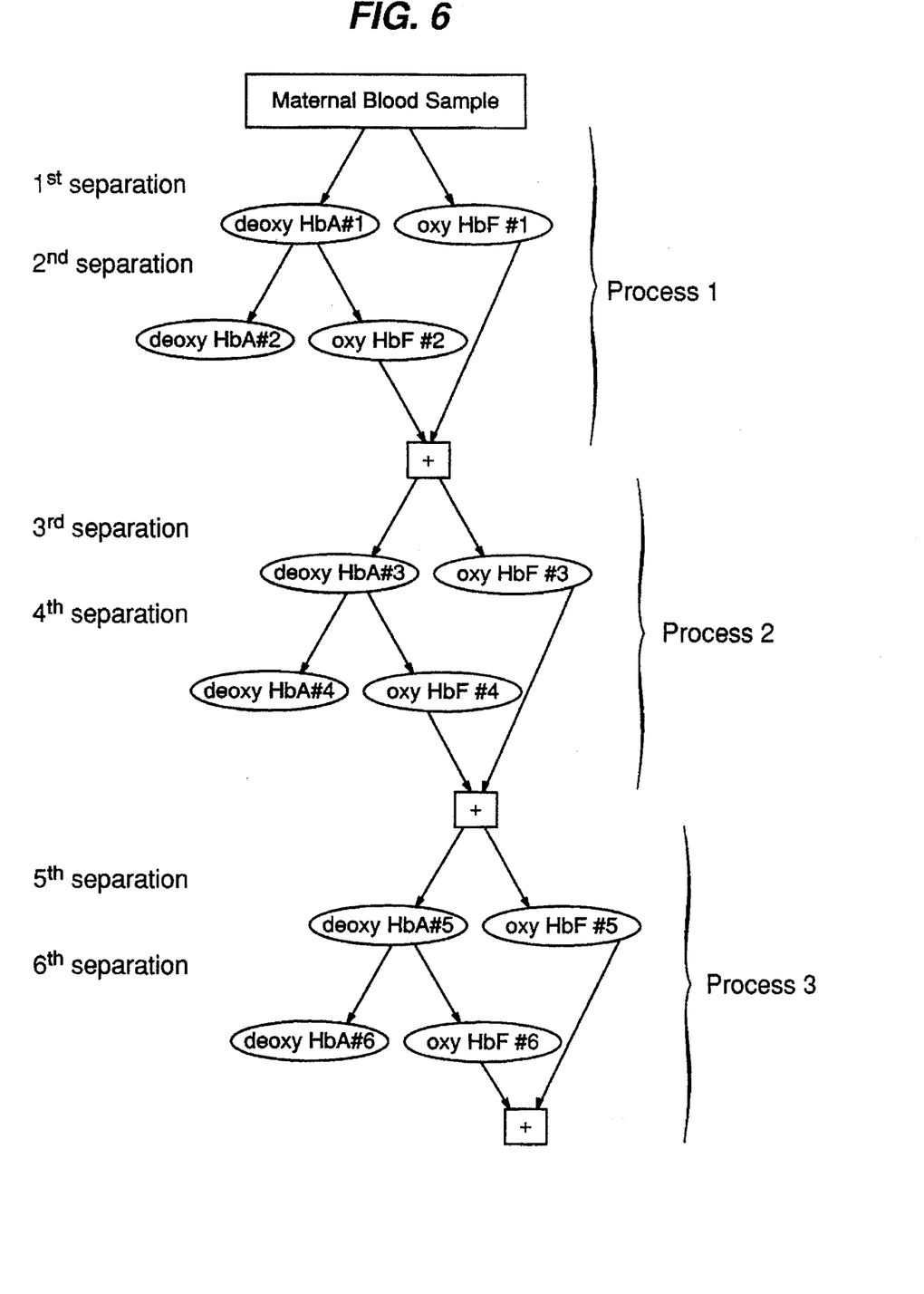
FIG. 6 is a flow diagram of the iterative procedure that could be used to maximize the number of maternal cells to be eliminated and minimizes the number of fetal cells that would be lost.

However at that point in the process neither the specificity nor the sensitivity is sufficient. That is the percent of maternal cells eliminated (the specificity) is not great enough and not enough fetal cells are retained (the sensitivity), respectively. In order to increase both the specificity and the sensitivity, we repeat the separation iteratively as follows (see FIG. 6): The deoxyHbA #1 aliquot is processed, further eliminating maternal cells while retaining more of the fetal cells, as aliquots deoxyHbA #2 and oxyHbF #2. We discard deoxyHbA #2 but combine oxyHbF#2 with oxyHbF #1, and repeat the separation. In this way we continue iteratively to work with the aliquots having the most retained fetal cells, as shown in FIG. 6.

Figure 7:
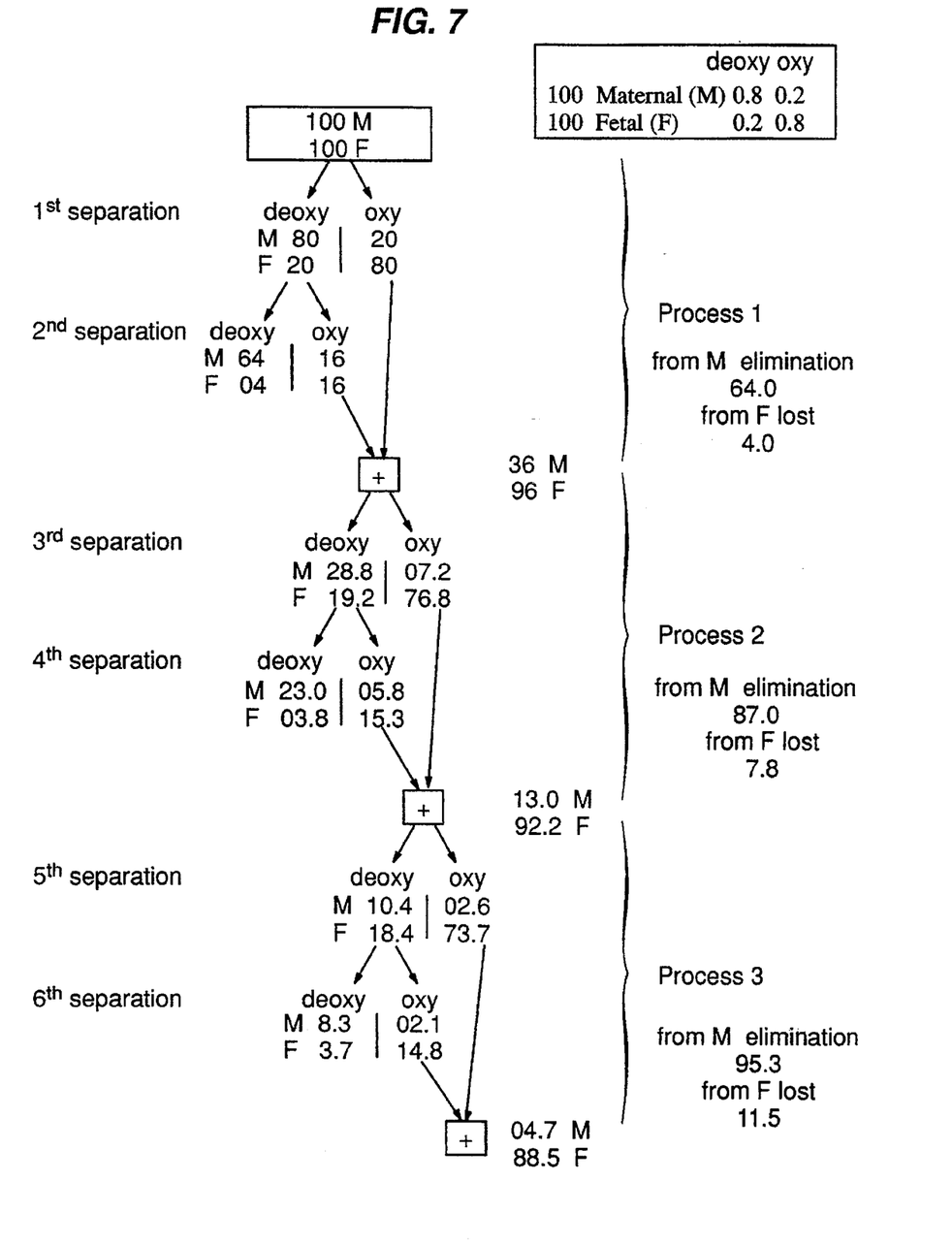
FIG. 7 is the same flow diagram of FIG. 6 but giving an numerical example of the maternal cells eliminated and the fetal cells retained.
Figure 8:
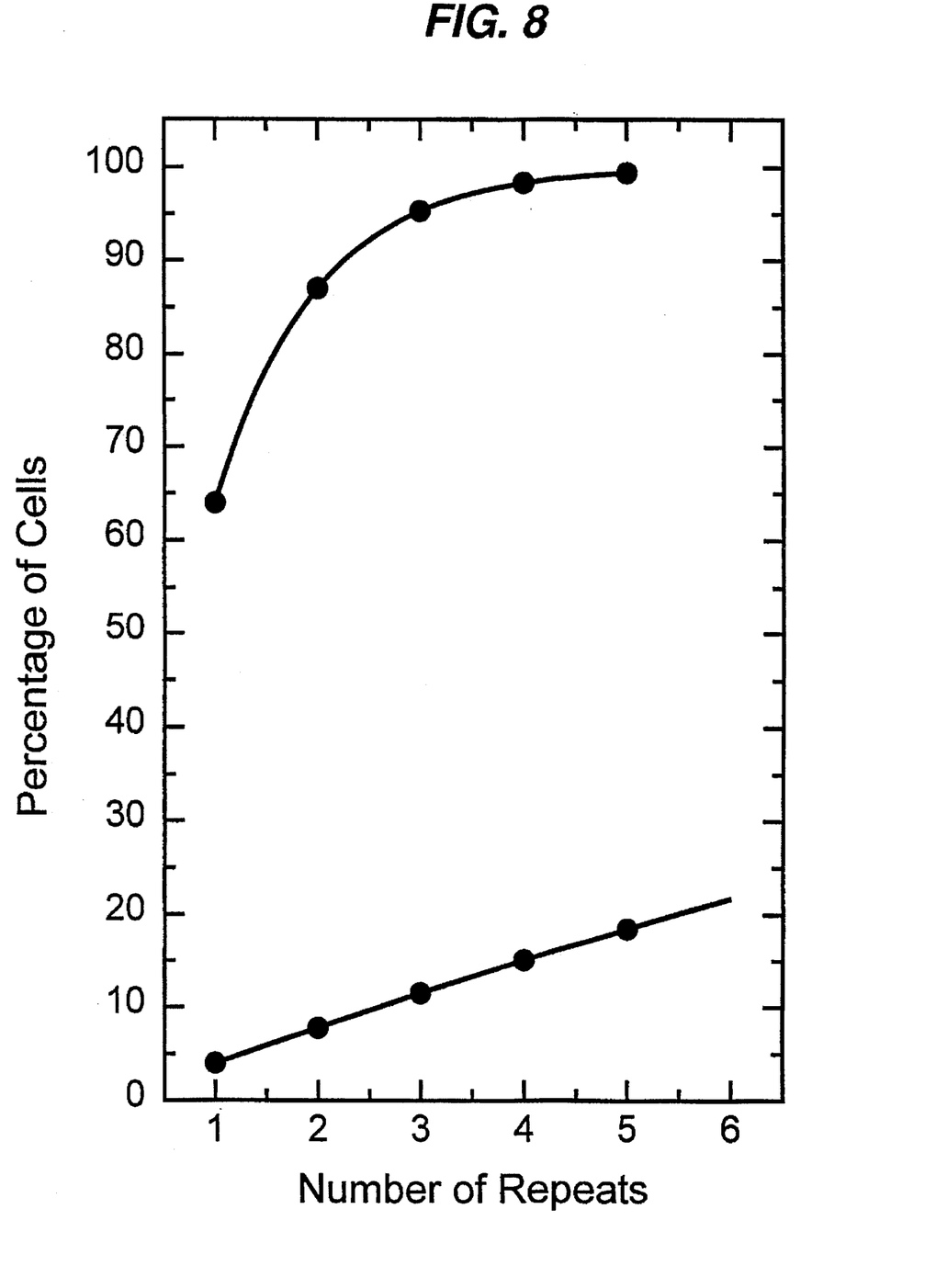
FIG. 8 illustrates the specificity (i.e. the percent of maternal cells eliminated, top curve) and the sensitivity (i.e. the percent of fetal cells lost, bottom curve) for the numerical example of FIG. 7 illustrating that in this case only three iterations would be useful.

In summary, we perform the separation only on the deoxyHbA #1 aliquot producing aliquots deoxyHbA #2 and oxyHbF #2. We add the aliquot oxyHbF #1 to the aliquot oxyHbF #2 and run that through the apparatus producing aliquots deoxyHbA #3 and oxyHbF #3. Next we perform the separation only on the deoxyHbA #3 to produce deoxyHbA #4 and oxyHbF #4. Next aliquot oxyHbF #4 is added to oxyHbF #3, and so forth. Each of these repetitions will continue to further the separation and increase the specificity and sensitivity of the method. FIG. 7 is a numerical illustration of the iterative separation method. The example is given on the assumption for calculational purposes only, that after each separation process, for the maternal nucleated cells, 20% of the HbA molecules are oxyHbA, and 80% of the HbA molecules are deoxyHbA, and for the fetal cells 80% of the HbF molecules are oxy HbF, and 20% of the HbF molecules are deoxyHbF. In FIG. 8 we graph the specificity and sensitivity for this case. Note from FIG. 8 that, in this case, it would probably not be efficacious to continue the process for more than three times.

I claim:

1. An apparatus for separating nucleated maternal red blood cells from nucleated fetal red blood cells in a blood sample, comprising:

(a) a means for chemically effectuating the O2 binding affinity of HbA molecules in maternal cells and of HbF molecules in fetal cells, of a blood sample;

whereby said means for chemically effectuating the O2 binding affinity of the HbA molecules in said maternal cells and of said HbF molecules in said fetal cells, of said blood sample creates an effectuated blood sample containing a larger proportion of deoxyHbA paramagnetic molecules than of oxyHbA non-paramagnetic molecules in said maternal cells and a larger proportion of oxyHbF non-paramagnetic molecules than of deoxyHbF paramagnetic molecules in said fetal cells;

(b) a magnetic field means;

whereby said magnetic field means is applied to the said effectuated blood sample for differentially applying a greater magnetic attraction to the maternal cells than to the fetal cells due to the said larger proportion of deoxyHbA paramagnetic molecules than oxyHbA non-paramagnetic molecules contained in the maternal cells and said larger proportion of the oxyHbF non-paramagnetic molecules than deoxyHbF paramagnetic molecules contained in the fetal cells, thereby moving said maternal cells away from said fetal cells to separate said maternal cells from said fetal cells, in said effectuated blood sample, thereby forming two aliquots, a first aliquot containing a greater proportion of said maternal cells and a second aliquot containing a greater proportion of said fetal cells, than was in the original said blood sample.

2. The apparatus of claim 1, wherein a means for iteratively reapplying said magnetic field means to said aliquot containing a greater proportion of said fetal cells is used to form succeeding aliquots with incrementally higher proportions of said fetal cells;

whereby the number of iterations executed by said means for iteratively reapplying said magnetic field is dependent on the proportion of said fetal cells versus said maternal cells desired.

3. The apparatus of claim 1, wherein said blood sample obtained from a pregnant woman.

4. The apparatus of claim 1, wherein an anticoagulation means is added to said blood sample.

5. The apparatus of claim 1, wherein said blood sample is held in a chamber.

6. The apparatus of claim 5, wherein said chamber consists of two pools, a first pool for concentrating said maternal cells, and a second pool for concentrating said fetal cells.

7. The apparatus of claim 5, wherein said chamber is vibrated to assist the motion of the cells being moved by said magnetic field means.

8. The apparatus of claim 5, wherein said chamber is made of a hydrophobic material to help prevent the nucleated blood cell from sticking to the sides of said container.

9. The apparatus of claim 2, wherein said aliquots containing a greater proportion of said maternal cells are exposed to said magnetic field means to create aliquots with higher proportions of said fetal cells than found in the prior maternal aliquots, and aliquots with higher proportions of said maternal cells than found in the prior maternal aliquots;

whereby said aliquots having a higher proportions of fetal cells than found in the prior maternal aliquots are combined with other aliquots with higher proportions of fetal cells from the maternal aliquots.

10. A process for separating nucleated maternal red blood cells from nucleated fetal red blood cells in a blood sample comprising:

(a) adding a chemical means to a blood sample to effectuate the O2 binding affinity of HbA molecules in said maternal cells and HbF molecules in said fetal cells;

whereby the effectuated blood sample contains a larger proportion of deoxyHbA paramagnetic molecules than of oxyHbA non-paramagnetic molecules in said maternal cells and a larger proportion of oxyHbF non-paramagnetic molecules than of deoxyHbF paramagnetic molecules in said fetal cells;

(b) applying a magnetic field means to said effectuated blood sample for differentially applying a greater magnetic attraction to the maternal cells than to the fetal cells due to said larger proportion of deoxyHbA paramagnetic molecules than oxyHbA non-paramagnetic molecules contained in the maternal cells and said larger proportion of the oxyHbF non-paramagnetic molecules than deoxyHbF paramagnetic molecules contained in the fetal cells, thereby moving the said maternal cells away from said fetal cells to separate said maternal cells from said fetal cells, in the said effectuated blood sample, thereby forming two aliquots;

wherein a first aliquot contains a greater proportion of said maternal cells and a second aliquot contains a greater proportion of said fetal cells, than was in the original said blood sample.

11. The process of claim 10, wherein a means for iteratively reapplying said magnetic field means to said aliquot containing a greater proportion of said fetal cells is used to form succeeding aliquots with incrementally higher proportions of said fetal cells;

whereby the number of iterations executed by said means for iteratively reapplying said magnetic field is dependent on the proportion of said fetal cells versus said maternal cells desired.

12. The process of claim 10, wherein said blood sample obtained from a pregnant woman.

13. The process of claim 10, wherein an anticoagulation means is added to said blood sample.

14. The process of claim 10, wherein said blood sample is held in a chamber.

15. The process of claim 14, wherein said chamber consists of two pools, a first pool for concentrating said maternal cells, and a second pool for concentrating said fetal cells.

16. The process of claim 14, wherein said chamber is vibrated to assist the motion of the cells being moved by said magnetic field means magnetic field.

17. The process of claim 14, wherein said chamber is made of a hydrophobic material to help prevent the nucleated blood cells from sticking to the sides of said container.

18. The process of claim 14, wherein said aliquots containing a greater proportion of said maternal cells are exposed to said magnetic field means to create aliquots with higher proportions of said fetal cells than found in the prior maternal aliquots, and said aliquots with higher proportions of said maternal cells than found in the prior maternal aliquots;

hereby said aliquots having a higher proportions of fetal cells are combined with other aliquots with higher proportions of fetal cells from the maternal aliquots.

* * * * *